United States Patent [19]

Telschow

[11] Patent Number: 4,564,687

[45] Date of Patent: Jan. 14, 1986

[54] PROCESS FOR PREPARING SUBSTITUTED PHTHALIC ANHYDRIDES

[75] Inventor: Jeffrey E. Telschow, Tarrytown, N.Y.

[73] Assignee: Stauffer Chemical Company, Westport, Conn.

[21] Appl. No.: 684,225

[22] Filed: Dec. 20, 1984

[51] Int. Cl.[4] ............................................. C07D 307/89
[52] U.S. Cl. ..................................... 549/240; 549/247
[58] Field of Search ......................................... 549/240

[56] References Cited

U.S. PATENT DOCUMENTS 2,264,429  12/1941  Bergmann et al. ................. 549/240
2,391,226  12/1945  Clifford et al. ...................... 549/240

Primary Examiner—Richard L. Raymond
Attorney, Agent, or Firm—Hensley M. Flash

[57] ABSTRACT

A process for preparing substituted phthalic anhydrides, e.g. 4-methylphthalic anhydride, in which the Diels-Alder addition product of a conjugated diene, e.g. isoprene, and maleic anhydride is reacted with sulfuryl chloride in the presence of pyridine and an optional solvent, e.g. chlorobenzene.

12 Claims, No Drawings

PROCESS FOR PREPARING SUBSTITUTED PHTHALIC ANHYDRIDES

BACKGROUND OF THE INVENTION

1. Field of the Invention

This invention relates to a process for preparing substituted phthalic anhydrides. More particularly, it relates to a process for preparing 4-methylphthalic anhydride.

2. Related Art

Phthalic anhydrides are valuable raw materials for making various useful products. These anhydrides are useful as intermediates in the chemical synthesis of herbicides and particularly in the synthesis of certain herbicides used to protect cereal crops. Other uses for these raw materials include polycyclic dyes, alkyd and epoxy resins, polyesters and plasticizers.

U.S. Pat. No. 2,391,226 (Clifford et al., Dec. 18, 1945) discloses addition products of chlormaleic anhydride and dichlormaleic anhydride prepared by the Diels-Alder reaction and the dehydrochlorination of these products in the presence of a catalyst, such as a secondary or tertiary amine. However, the six carbon ring is usually only partially dehydrogenated yielding a substituted dihydrophthalic anhydride.

U.S. Pat. No. 2,264,429 (Bergman, Dec. 2, 1941) discloses a process for preparing substituted phthalic anhydride in a single reaction. This reaction involves the combination of the condensation reaction between a diene and maleic anhydride and the dehydrogenation reaction. This combination is achieved by carrying out the condensation reaction in nitrobenzene or another nitrated aromatic substance, which not only acts as a diluent, but also as a dehydrogenating agent by reducing itself and giving the corresponding amine. This patent discloses o-nitrotoluene as another example of a nitrated aromatic substance useful in the disclosed process.

SUMMARY OF THE INVENTION

A process for preparing substituted phthalic anhydrides in good yields would be advantageous because of the various useful products that are prepared from these anhydrides. It is an object of the present invention to provide a unique, cost-effective process for the preparation of substituted phthalic anhydrides. Other objects and advantages of the present invention are shown throughout the specification.

In accordance with the present invention, it has now been discovered that substituted phthalic anhydrides can be prepared by a process which comprises reacting the Diels-Alder addition product of a conjugated diene and maleic anhydride with sulfuryl chloride in the presence of pyridine.

DETAILED DESCRIPTION OF THE INVENTION

The substituted phthalic anhydrides prepared by the processes of this invention can include a substituent or the lack of a substituent at each of the four available sites on the benzene ring, that is the 3, 4, 5 and 6 carbon positions. These optional substituents can be quite varied as they do not actively enter into the reactive steps included in the processes of this invention. These substituents, for example, can be selected from the group consisting of $C_1$ to $C_{10}$ alkyl, $C_6$ to $C_{14}$ aryl and $C_1$ to $C_{16}$ aralkyl and wherein the alkyl, aryl and aralkyl substituents are optionally substituted with one or more halogen, cyano and/or carboxylic groups. A preferred substituted phthalic anhydride is 4-methylphthalic anhydride.

The process can use the Diels-Alder addition product as a starting material or can comprise a first step of actually preparing this addition product. The Diels-Alder addition product can be derived from other than the Diels-Alder reaction. In addition, the double bond isomers of the Diels-Alder addition product can be used in the process of this invention.

The Diels-Alder addition products of this invention are formed by reacting maleic anhydride with a conjugated diene. The conjugated diene can include butadiene, 2,3-dimethylbutadiene, other substituted butadienes and preferably isoprene.

The addition product can be prepared by reacting the maleic anhydride with the conjugated diene in a nitrogen atmosphere. This reaction can be run with or without a solvent. When no solvent is used, the maleic anhydride is usually heated until it melts, then the conjugated diene is added slowly under the surface of the melt. When a solvent is used, the solvent is added to the maleic anhydride and the resulting mixture heated to from about 40° C. to 50° C. prior to the addition of the diene. When the addition of the diene is completed, the reactants can then be heated to a reaction temperature of from about 50° C. up to about 120° C. with temperatures in the upper end of the range from about 100° C. up to about 120° C. being preferred. The reactants are kept within the reaction temperature range until the reaction is completed, usually for about one hour. The reaction can be exothermic, therefore external cooling can be required to maintain the reactants within the reaction temperature range.

The stoichiometry of this Diels-Alder addition reaction usually involves one mole of the maleic anhydride reacting with one mole of the conjugated diene to produce one mole of the addition product, therefore it is economically desirable to react equimolar quantities of the reactants. However, a fractional molar excess of the diene is usually used to ensure that all the maleic anhydride is consumed in the reaction.

After the reaction to form the addition product is completed, excess diene can be stripped from the reaction zone under vacuum at a pressure which minimizes sublimation of the addition product and distillation of the solvent, if any is present.

The reaction used to prepare the addition product can take place in the presence or absence of an appropriate solvent. Such a solvent can be, for example, chlorobenzene, hydrocarbons like hexane and heptane, dimethylformamide, or any of the other solvents disclosed in the literature. However, in the further steps of this process, the solvent used therein should not be reactive with the sulfuryl chloride reactant, therefore a solvent like dimethylformamide would be inappropriate. A particularly preferred solvent for use in all the steps of this process is chlorobenzene.

The reaction of the addition product with sulfuryl chloride in the presence of pyridine can be carried out directly upon the addition product/solvent solution after the excess diene is stripped from the reaction zone. The usual mode of addition is to first add the pyridine to the addition product/solvent solution then add the sulfuryl chloride slowly over a period of time.

The stoichiometry of this reaction usually involves one mole of the Diels-Alder addition product reacting with two moles of sulfuryl chloride and four moles of pyridine to produce one mole of the substituted phthalic anhydride, therefore it is economically desirable to react quantities of the reactants in as close to the stoichiometric ratio as possible. However, a fractional molar excess of sulfuryl chloride and pyridine is usually used to ensure that all the Diels-Alder addition product is consumed in the reaction.

The addition of pyridine to the addition product/solvent solution can take place at various temperatures. However, room temperature or below is preferred as the subsequent addition of sulfuryl chloride to this reaction mixture preferably takes place at low temperatures ranging from about $-10°$ C. to about 35° C. with a more preferred range of from about $-10°$ C. to about 10° C. After the addition of the sulfuryl chloride is completed, the temperature of the reaction mixture can be raised, preferably slowly, to a reflux temperature of generally about 130° C. (depending on the solvent used).

It is theorized that the sulfuryl chloride chlorinates the Diels-Alder addition product which is in turn dehydrochlorinated by the pyridine to a substituted phthalic anhydride. The particular anhydride formed is dependent upon the choice of the initial reactants. Sulfur dioxide is liberated and pyridine hydrochloride forms. The reactants are preferably kept refluxing until the reaction is completed, usually about 2 hours.

The resulting substituted phthalic anhydride product can be extracted by a water/solvent extraction step, preferably water/chloroform, and purified by distillation.

In a preferred mode of the process of this invention, 4-methylphthalic anhydride (4-MPA) is prepared. This preparation comprises reacting isoprene and maleic anhydride to form 4-methyl-1,2,3,6-tetrahydrophthalic anhydride (4-MTPA), then reacting this product with sulfuryl chloride in the presence of pyridine to form 4-MPA.

In another preferred embodiment, 4-MPA is prepared directly from the intermediate 4-MTPA without the first step of forming that intermediate. In both these embodiments, the use of a solvent is preferred and chlorobenzene is particularly favored.

The following example describes various embodiments of the invention. Other embodiments will be apparent to one of ordinary skill in the art from a consideration of this specification or practice of the invention disclosed herein. It is intended that the specifications and example be considered as exemplary only with the true scope and spirit of the invention being indicated by the claims which follow the example.

EXAMPLE

In a 1 liter 3-necked flask fitted with a dropping funnel, a mechanical stirrer, a pot thermometer, a nitrogen inlet and a reflux condenser was placed 98.1 grams (1.0 mole) of maleic anhydride and 100 milliliters of chlorobenzene. The mixture was heated under a head of nitrogen to 40° C.–50° C. Isoprene (75.0 grams, 1.1 moles) was then added dropwise to the flask below the surface of the mixture, using an extension tube of TEFLON fluorocarbon polymer attached to the dropping funnel, at such a rate as to minimize the reflux. The temperature of the reactants in the flask was controlled with intermittent cooling using a cold water bath and kept between 50° and 100° C.

After the addition of the isoprene was completed, the contents of the reactor flask was maintained at 70°–100° C. for 60 minutes to ensure complete reaction then cooled to 40° C. Excess isoprene was removed from the reactor as the pressure was reduced to 50 mm Hg.

The resulting clear, nearly colorless solution of 4-methyl-1,2,3,6-tetrahydrophthalic anhydride (4-MTPA) was diluted with 325 milliliters of chlorobenzene and 330 milliliters (4.08 moles) of pyridine. The nitrogen inlet on the reactor flask was replaced with an outlet connected to a caustic trap. This reaction mixture was cooled to 0° C. in a dry ice/acetone bath.

Sulfuryl chloride (276 grams, 2.04 moles) was added dropwise while maintaining a reactor temperature of from $-10°$ C. to 10° C. The color of the reacting mixture deepened to a dark brown during the addition and pyridine hydrochloride precipitated. After the addition of sulfuryl chloride was completed, the reactor temperature was slowly increased to reflux at 130° C. Gas evolution slowly began at 50° C. and became vigorous by 100° C.

After 2 hours of refluxing, the reactor was cooled to 25° C., 500 milliliters of water was added, and the liquids were decanted to remove some tar and solids. The residue remaining in the reactor was again treated with 500 milliliters of water and 300 milliliters of chloroform was added. The resulting layers were separated and the combined aqueous layers were extracted once more with 300 milliliters of chloroform. The combined organic phases were distilled under reduced pressure and the residue was distilled through an uncooled still-head at 106° C.–110° C./1.4 mm Hg. as a yellow liquid 4-methylphthalic anhydride (4-MPA, 59.8 grams, 37 weight percent yield based on maleic anhydride) which later crystallized (melting point 80°–89° C.). The 4-MPA was confirmed by proton NMR analysis and found to be 97 percent pure by gas chromatography.

What is claimed is:

1. A process for preparing a substituted phthalic anhydride which comprises reacting the Diels-Alder addition product of a conjugated diene and maleic anhydride with sulfuryl chloride in the presence of pyridine.

2. The process of claim 1 wherein said conjugated diene is isoprene.

3. The process of claim 1 wherein the reaction is carried out in the presence of a solvent.

4. The process of claim 8 wherein the solvent is chlorobenzene.

5. A process for preparing 4-methylphthalic anhydride which comprises reacting 4-methyl-1,2,3,6-tetrahydrophthalic anhydride with sulfuryl chloride in the presence of pyridine and a solvent.

6. The process of claim 5 wherein the solvent is chlorobenzene.

7. A process for preparing a substituted phthalic anhydride which comprises:
   (a) reacting a conjugated diene and maleic anhydride to form a Diels-Alder addition product;
   (b) reacting the addition product with sulfuryl chloride in the presence of pyridine.

8. The process of claim 7 wherein steps (a) and (b) are carried out in the presence of a solvent.

9. The process of claim 8 wherein the solvent is chlorobenzene.

10. The process of claim 7 wherein the diene is isoprene.

11. A process for preparing 4-methylphthalic anhydride which comprises:
(a) reacting isoprene and maleic anhydride in the presence of a solvent to form 4-methyl-1,2,3,6-tetrahydrophthalic anhydride;
(b) reacting the 4-methyl-1,2,3,6-tetrahydrophthalic anhydride with sulfuryl chloride in the presence of pyridine and a solvent.

12. The process of claim 11 wherein the solvent is chlorobenzene.

* * * * *

UNITED STATES PATENT AND TRADEMARK OFFICE
CERTIFICATE OF CORRECTION

PATENT NO. : 4,564,687

DATED : January 14, 1986

INVENTOR(S) : Jeffrey E. Telschow

It is certified that error appears in the above—identified patent and that said Letters Patent is hereby corrected as shown below:

Claim 4, change "claim 8" to "claim 3".

Signed and Sealed this

Eleventh Day of March 1986

[SEAL]

Attest:

DONALD J. QUIGG

*Attesting Officer*     *Commissioner of Patents and Trademarks*